United States Patent [19]

Altadonna

[11] Patent Number: 5,505,768

[45] Date of Patent: Apr. 9, 1996

[54] HUMIDITY MOISTURE EXCHANGER

[76] Inventor: Anthony J. Altadonna, 2750 Hamilton Ct. West, Mobile, Ala. 36695

[21] Appl. No.: 320,951

[22] Filed: Oct. 11, 1994

[51] Int. Cl.$^6$ ............................ B01D 29/96; B01D 53/02
[52] U.S. Cl. ................... 96/108; 96/149; 96/150; 55/422; 55/357
[58] Field of Search ................... 96/108, 123, 149, 96/150; 55/309, 328, 356, 357, 422; 210/470

[56] References Cited

U.S. PATENT DOCUMENTS

| | | | |
|---|---|---|---|
| 2,453,206 | 11/1948 | Donat | 55/357 |
| 3,788,484 | 1/1974 | Godin | 210/470 X |
| 3,823,532 | 7/1974 | Cooper et al. | 55/422 X |
| 4,334,896 | 6/1982 | Müller | 55/422 X |
| 4,376,053 | 3/1983 | Bullock et al. | 210/470 X |
| 4,386,948 | 6/1983 | Choksi et al. | 55/499 |
| 4,529,420 | 7/1985 | Norbäck | 96/123 |
| 4,546,778 | 10/1985 | Sullivan | 128/718 |
| 4,673,386 | 6/1987 | Gordon | 604/48 |
| 5,109,471 | 4/1992 | Lang | 392/396 |
| 5,135,489 | 8/1992 | Jepson et al. | 604/48 |
| 5,238,052 | 8/1993 | Chagnot | 96/150 X |
| 5,320,096 | 6/1994 | Hans | 128/205.29 |

FOREIGN PATENT DOCUMENTS

| | | |
|---|---|---|
| 0265163 | 4/1988 | European Pat. Off. . |
| 0462412 | 12/1991 | European Pat. Off. . |
| 2231509 | 11/1990 | United Kingdom . |
| WO88/09205 | 12/1988 | WIPO . |
| WO91/19527 | 12/1991 | WIPO . |

*Primary Examiner*—Robert Spitzer
*Attorney, Agent, or Firm*—Richard Litman

[57] ABSTRACT

A humidity moisture exchanger (HME) for trapping heat and/or moisture normally lost during mechanical ventilation and the like. This HME includes a housing having a first chamber and a second chamber. The second chamber includes a pair of fluid ports connectable, in series, to a fluid flow tube extending from the patient. Inside the housing is a filter or an absorbent heat and moisture collecting material. To permit the uninhibited passage of fluid through the housing, the absorbent material is removed from the second chamber area and temporarily stored within the first chamber area.

18 Claims, 5 Drawing Sheets

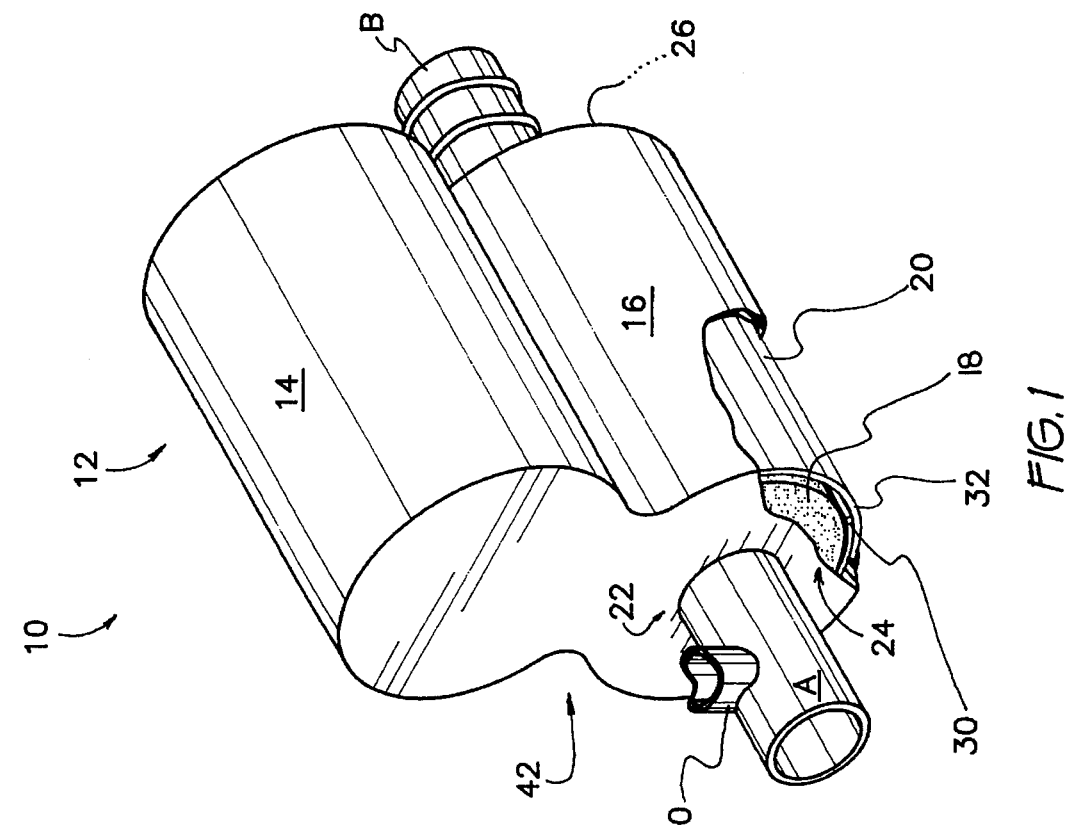
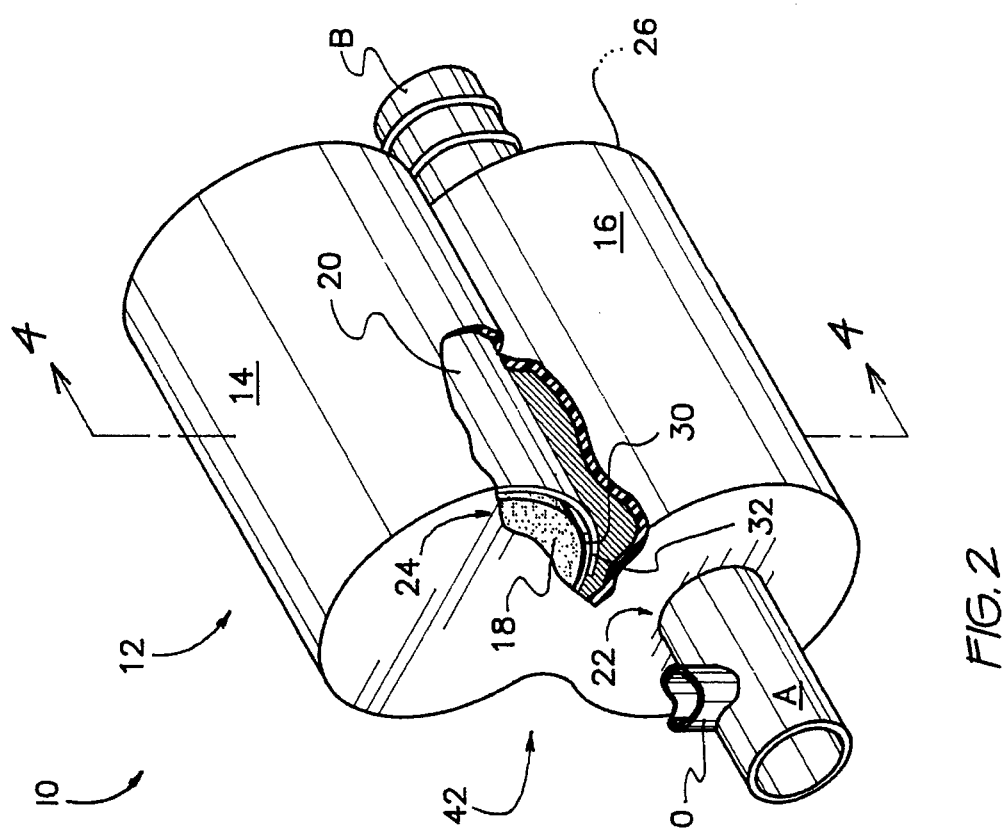

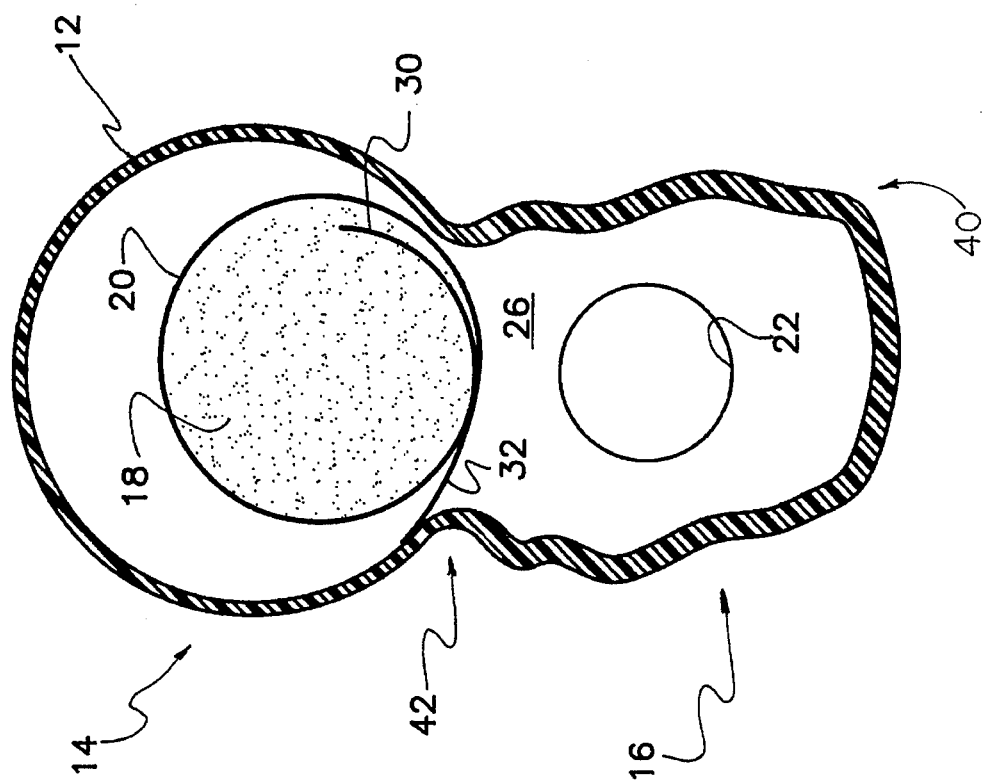
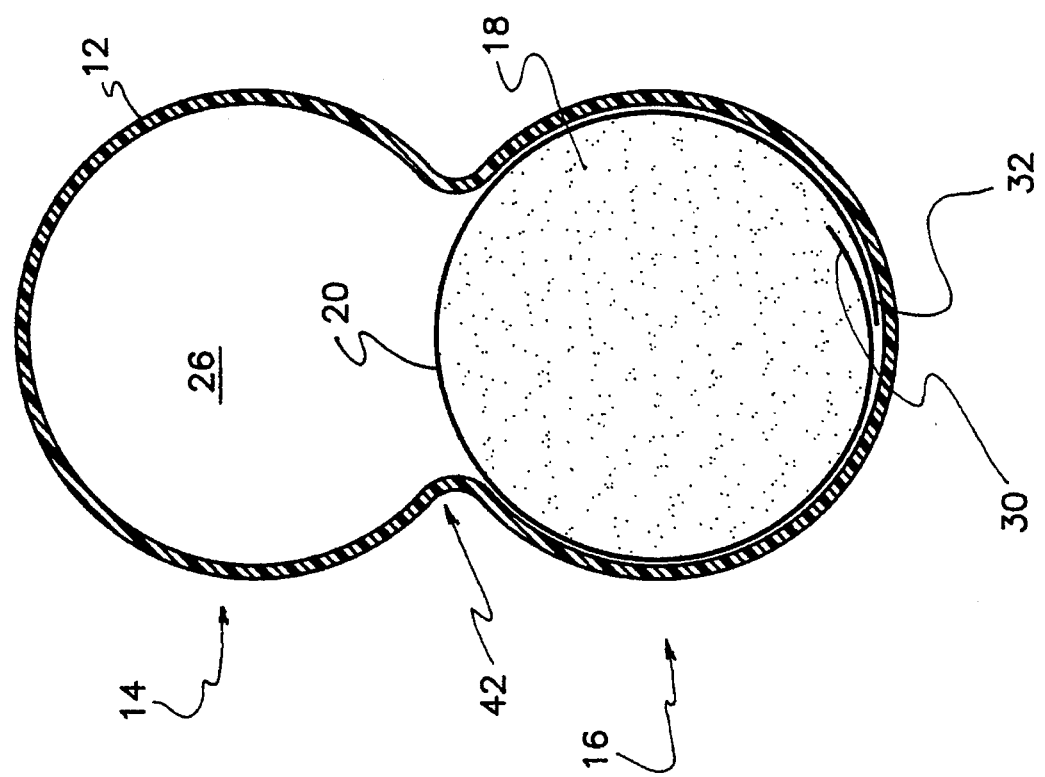

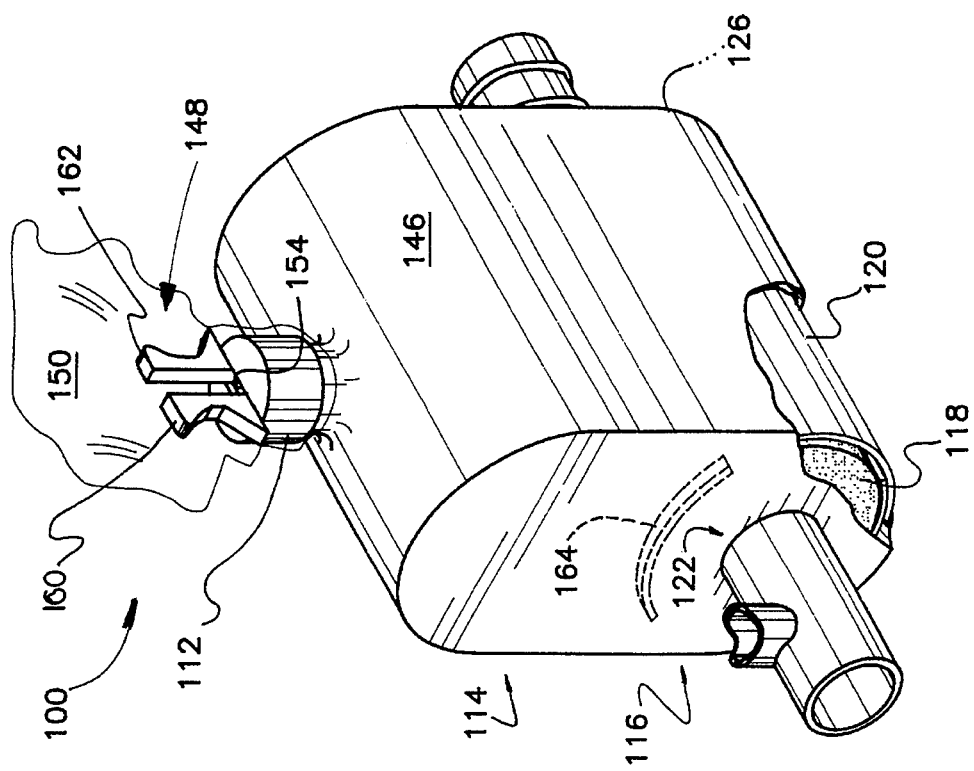
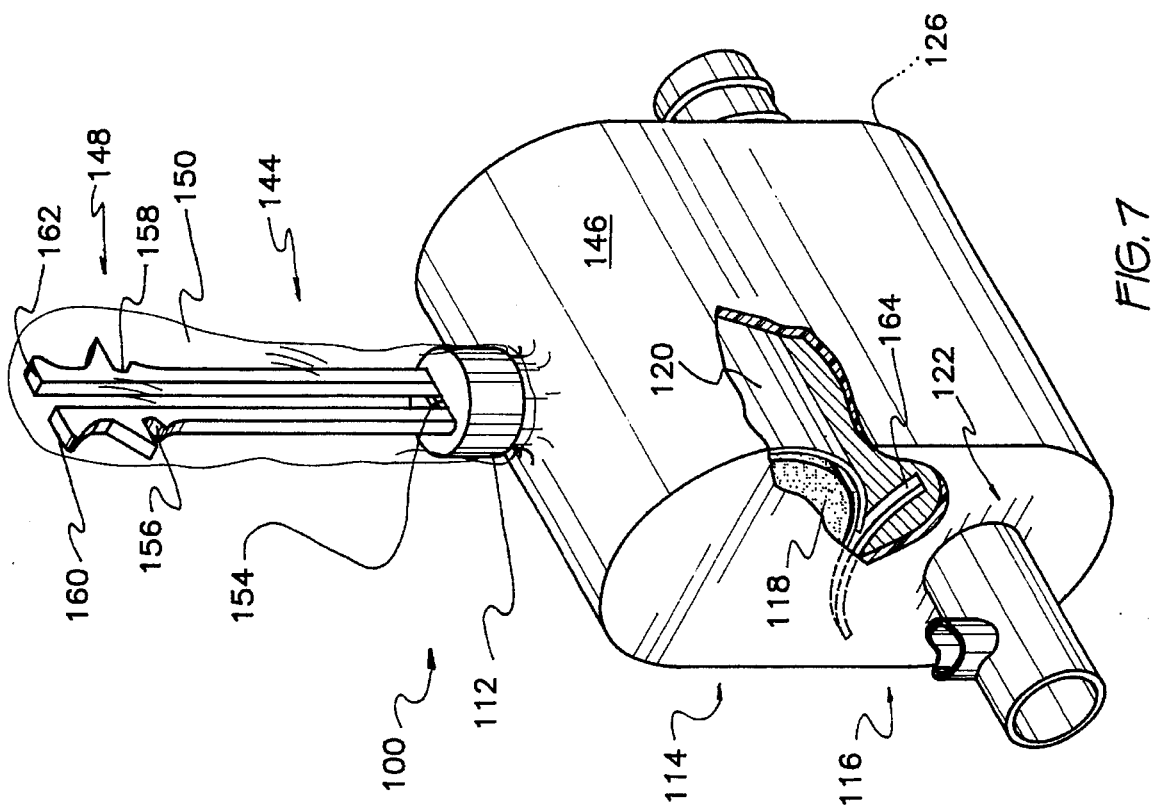

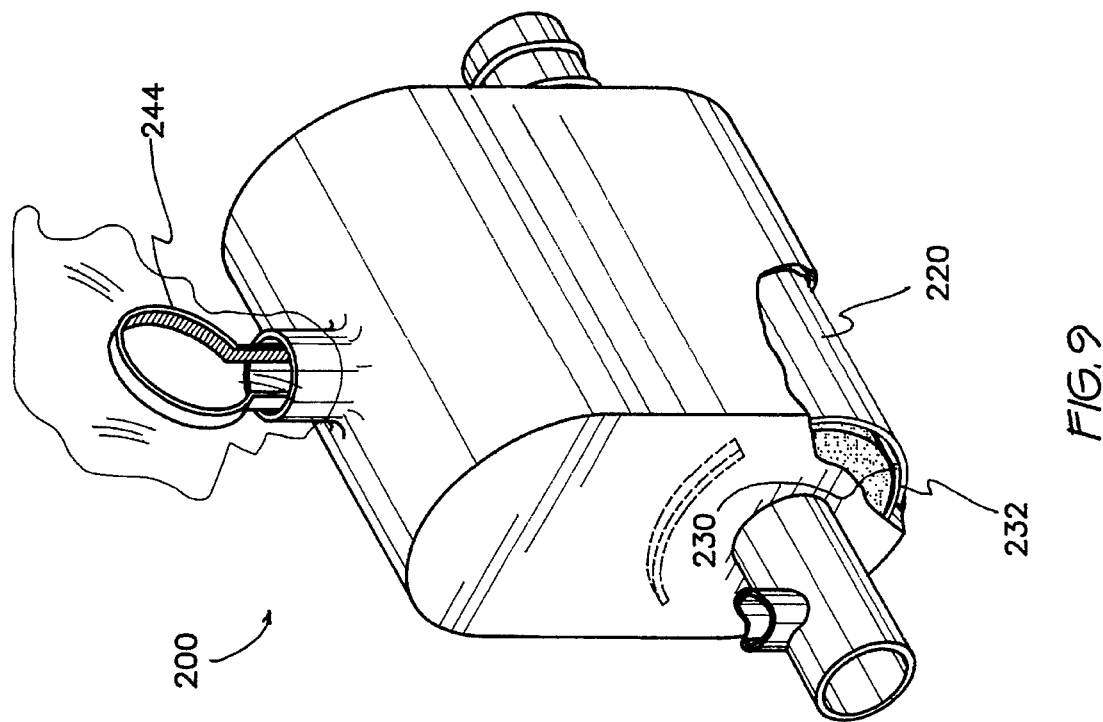
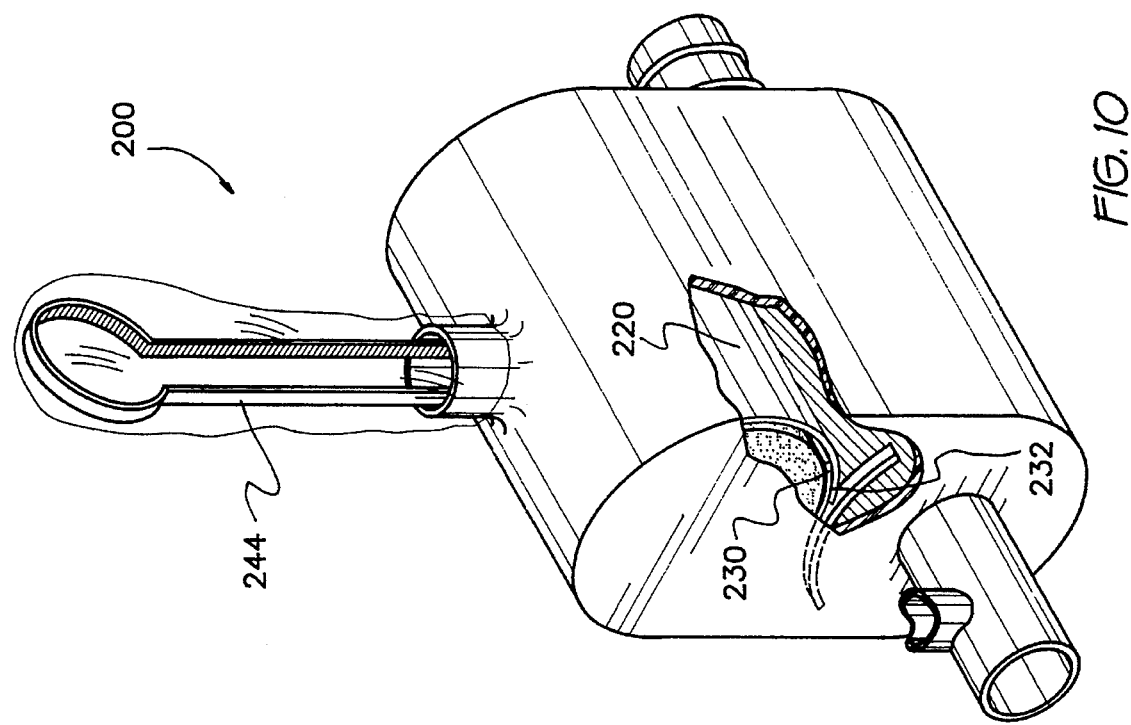

HUMIDITY MOISTURE EXCHANGER

BACKGROUND OF THE INVENTION

1. Field of the Invention

The present invention relates to a humidity moisture exchanger (HME) usable in conjunction with a standard ventilator machine or the like. More specifically, the present invention relates to an HME capable of permitting the uninhibited passage of fluid, including gasses and aerosols, without being detached from the ventilator circuit.

2. Description of the Prior Art

It is common to place a Humidity Moisture Exchanger (HME) within a tube connecting a patient to a ventilator machine or the like. The HME becomes a part of the ventilator circuit, and it acts as a filtering mechanism to trap heat and moisture that would otherwise be lost during the artificial ventilation. The use of an HME is especially prevalent for patients utilizing endotracheal or tracheostomy tubes.

One invention pertaining to a filtering mechanism for a respiratory breathing system is disclosed in UK Patent Application GB 2 231 509 A, published on Nov. 21, 1990. The filtering mechanism of this invention includes a housing having an inlet port and an outlet port. This housing is constructed from two parts, each including an inner peripheral wall. When the two parts of the housing are affixed together, a filter member is secured between the inner peripheral walls of each part. During use of the respiratory breathing system, the filter member remains in a position directly in the path of air traveling between the inlet and outlet ports of the housing.

A similar device is illustrated in European Patent Application No. 0 265 163 A2 published on Apr. 27, 1988. This device is a heat and moisture exchanger having first and second ports secured together to form a housing. An air passageway is created by inlet and outlet ports integral with the housing. A filter member is affixed within the housing so as to permanently block the air passageway.

Another similar device is disclosed in International Patent Application No. WO 91/19527 published on Dec. 26, 1991. This invention is a device to be incorporated in the medical duct supplying air and/or gasses to a patient. It includes a filter member permanently affixed between inlet and outlet portions of a housing. A resistance is positioned within a metal sleeve spaced from the filter member. This resistance is utilized to control both the temperature and the humidity of the air passing through the filter member.

One problem with the above filtering mechanisms is that they block the passage of aerosols or other medications passed to the patient through the ventilator circuit. Therefore, to adequately pass aerosols and medications to the client, it is necessary to completely remove the filtering mechanism from the ventilator circuit. Such removal results in an undesired pressure drop within the ventilator circuit, and it increases the likelihood of a passage of contaminants either to or from the patient.

A non-filtering mechanism relevant to the instant invention is U.S. Pat. No. 4,673,386, issued to Mark G. Gordon on Jun. 16, 1987. This patent discloses a blood sampler device having a housing with first and second ports. The first port is connectable to a patient blood supply, and the second port is connectable to the injection site. Retractably positioned within the housing is a piston attached to a sealing member, which may be positioned to impede the passage of fluid through the housing.

None of the above inventions and patents, taken either singly or in combination, is seen to describe the instant invention as claimed.

SUMMARY OF THE INVENTION

The present invention relates to a humidity moisture exchanger (HME) for trapping heat and/or moisture normally lost during mechanical ventilation and the like. This HME includes a housing having a first chamber and a second chamber. The second chamber includes a pair of fluid ports connectable, in series, to a fluid flow tube extending from the patient. Inside the housing is an absorbent heat and moisture collecting material surrounded by a fluid impermeable enclosure. This enclosure has a pair of open ends that align with the fluid flow ports of the housing when the enclosure is in the second chamber area. To permit the uninhibited passage of aerosol through the housing, the enclosure, with the absorbent material therein, is removed from the second chamber area and temporarily stored within the first chamber area. A sealing engagement between the enclosure and the housing interior confines possible areas of fluid flow, thereby minimizing areas of dead space within the housing.

Accordingly, it is a principal object of the invention to provide a novel HME for trapping heat and/or moisture normally lost during mechanical ventilation and the like.

It is another object of the invention to provide a novel HME having an absorbent material that is removable from the passageway of fluid travelling through the HME.

It is a further object of the invention to provide a novel HME that minimizes dead space.

Still another object of the invention is to provide a novel HME having an uncomplicated design.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 1 is a perspective view, having a partial section broken away, of a first configuration of a first embodiment of the humidity moisture exchanger of the invention.

FIG. 2 is a perspective view, having a partial section broken away, of a second configuration of the humidity moisture exchanger shown in FIG. 1.

FIG. 3 is a cross sectional view of three different configurations of a first embodiment of the absorbent material and encasing of the present invention.

FIG. 4 is a cross sectional view of the humidity moisture exchanger shown in FIG. 1.

FIG. 5 is a cross sectional view of the humidity moisture exchanger shown in FIG. 1, illustrating movement of the encasing.

FIG. 6 is a perspective view, having a partial section broken away, of a first configuration of a second embodiment of the humidity moisture exchanger of the invention.

FIG. 7 is a perspective view, having a partial section broken away, of a second configuration of the humidity moisture exchanger shown in FIG. 6.

FIG. 8 is a cross sectional view of a second embodiment of the absorbent material and encasing of the invention.

FIG. 9 is a perspective view, having a partial section broken away, of a first configuration of a third embodiment of the humidity moisture exchanger of the invention.

FIG. 10 is a perspective view, having a partial section broken away, of a second configuration of the humidity moisture exchanger shown in FIG. 9.

Similar reference characters denote corresponding features consistently throughout the attached drawings.

DETAILED DESCRIPTION OF THE PREFERRED EMBODIMENTS

Figure 3:
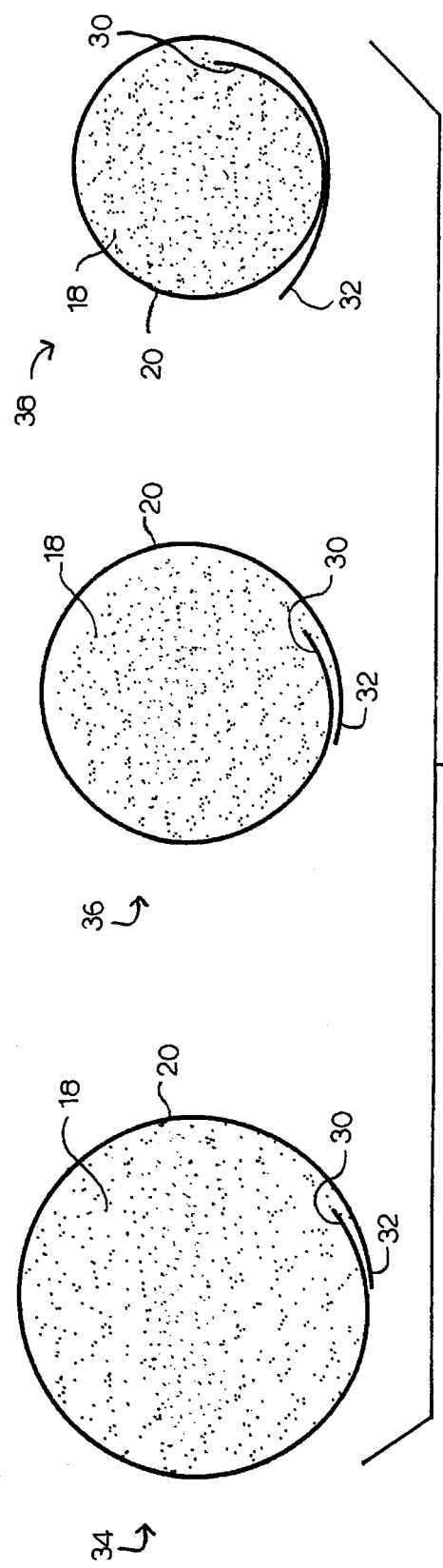

One embodiment of the Humidity Moisture Exchanger (HME) of the invention is illustrated in FIG. 1. This HME 10 includes a housing 12 having a first chamber area 14 and a second chamber area 16 in fluid communication with each other. Positioned within second chamber area 16 is an absorbent material 18 surrounded by a fluid impermeable encasing 20. A first port 22 formed within second chamber area 16 is aligned with a first opening 24 formed within encasing 20. Likewise, surface 26 of housing 12 includes a second port (not shown) formed within second chamber area 16. This second port is alignable with a second opening (not shown) formed within encasing 20.

As illustrated in FIG. 1, a pair of tubes A,B are extending from first port 22 and the second port. Tube A is for connection to a ventilator or similar apparatus (not shown), and it includes an offshoot O to which a carbon dioxide monitor (not shown), or the like, can be attached. Tube B is for transporting fluid between second chamber area 16 and the patient.

Fluid, such as gasses and aerosols, can enter second chamber area 16 from either tube A or tube B. If HME 10 is connected to a ventilator circuit, fluid enters second chamber area 16 from tube A when the patient inhales. This fluid travels through absorbent material 18 and then is carried to the patient via tube B. When the patient exhales, fluid travels from the patient, through tube B, into second chamber area 16, through absorbent material 18, and into tube A.

For apparatuses such as a ventilator, in the absence of a system to produce or collect heat and moisture, heat and moisture are commonly lost during each exhalation by the patient. When HME 10 is connected to the ventilator circuit, absorbent material 18 acts as an "artificial nose" that traps heat and moisture from fluid passing through second chamber area 16. Additionally, absorbent material 18 may act as a filter to prevent dirt particles and the like from passing through tube B into communication with the patient. Suitable materials for absorbent material 18 include hygroscopic, hydrophobic, and hydrophilic materials, as well as other materials known in the art.

As shown in FIG. 2, encasing 20 and absorbent material 18 are movable from second chamber area 16 into first chamber area 14. As there is a substantially sealing engagement between encasing 20 and housing 12, fluid within second chamber 16 is prevented from entering first chamber area 14. Therefore, absorbent material 18 does not affect the fluid flowing between tube A and tube B.

The movement of absorbent material 18 out from the fluid passageway between tube A and tube B is important during the application of medications, aerosols, and the like. These medications and aerosols are commonly supplied to the patient through the ventilator circuit. If there is an absorbent material located between the patient and the point where the medication or aerosol is introduced into the ventilator circuit, the medication or aerosol will be either partially or entirely consumed by the absorbent material. Hence, the medication or aerosol will not adequately reach the patient.

In prior art HME's that do not have an absorbent material capable of being movable out from the passage of fluid, the entire HME must be detached from the ventilator circuit. This temporarily opens the ventilator circuit, increasing the likelihood that the positive pressure in the ventilator circuit will undesirably fall to ambient pressure. Opening the ventilator circuit also increases the likelihood that germs and other contaminants could either enter the components of the circuit or travel from the ventilator circuit to a nearby health care provider.

As illustrated in FIG. 3, encasing 20 is substantially arcuate or tubular, and it includes a pair of free ends 30,32. In this figure, there is illustrated various configuration of encasing 20. The configuration labelled 34 shows encasing 20 in an uninhibited or resting state, and the configurations labelled 36,38 each show encasing 20 in a contracted position. Configuration 36 is partially contracted, and configuration 38 is fully contracted.

Each chamber area 14,16 confines encasing 20 such that it remains in the partially constricted configuration labelled 36 in FIG. 3. As encasing 20 is fabricated from a resilient material, it attempts to return to the resting or uninhibited configuration labelled 34. This attempted return causes encasing 20 to press against the interior of the chamber area, 14 or 16, within which it is positioned. This creates a sealing engagement between encasing 20 and the respective chamber area 14 or 16. When encasing 20 is within first chamber area 14, the sealing engagement prevents fluid from entering first chamber 14, therefore minimizing potential dead space within housing 12.

In FIG. 4, encasing 20 is illustrated within second chamber area 16. To move encasing 20 into first chamber area 14, second chamber area 16 is pinched or compressed at location 40, as illustrated in FIG. 5. This causes encasing 20 to change from the partially constricted configuration 36 to the fully constricted configuration 38 (see FIG. 3). In this fully constricted configuration 38, encasing 20 is capable of traveling through the captive opening 42, and into first chamber area 14. Once inside first chamber area 14, encasing 20 returns to the partially constricted configuration 36. To return encasing 20 to second chamber area 16, first chamber area 14 is pinched or compressed (not shown) in a manner similar to that of second chamber area 16 in FIG. 5.

As only pinching or compressing is necessary to move encasing 20 back and forth between chamber areas 14,16, the design of HME 10 is extremely uncomplicated. This design minimizes manufacturing costs, which is especially important for HME's, as they are commonly discarded after only a short period of time. That encasing 20 is moved without plungers or rods extending into housing 12 assures that housing 12 remains a closed system.

An alternate embodiment of the invention is illustrated in FIGS. 6 and 7. This HME 100 does not include a captive opening similar to opening 42, and it utilizes a plunger 144 to move encasing 120 and absorbent material 118 back and forth between first chamber area 114 and second chamber area 116. Plunger 144 extends through housing cap 112, and has a first end (not shown) affixed to encasing 120, and a second end 148 extending outward from housing cap 112. When plunger 144 is partially extended from housing cap 112, as illustrated in FIG. 6, encasing 120 is positioned within second chamber area 116. When plunger 144 is fully extended from housing cap 112, as illustrated in FIG. 7, encasing 120 is positioned within first chamber area 114. A plastic bag 150 extends from housing cap 112 and surrounds plunger 144. This prevents contamination within housing 146, and makes it a closed system.

To maintain plunger 144 in the partially extended position, second end 148 of plunger 144 lockingly engages housing cap 112. The mechanism for the locking engagement is illustrated in FIGS. 6 and 7, and is a pinch/catch mechanism. The part of housing cap 112 forming aperture 154, through which plunger 144 passes, is received within a pair of recessed portions 156,158 formed within plunger 144. Although not shown, a pair of flanges could be attached to housing cap 112 for extending into recessed portions 156,158. These recessed portions would increase the strength of the locking engagement between plunger 144 and housing cap 112. To disengage the locking engagement between plunger 144 and housing cap 112, the members 160,162 of plunger 144 are squeezed together, and second end 148 is displaced away from housing cap 112.

As shown in FIG. 7, there is no pinch/catch mechanism to maintain plunger 144 in its fully extended position. Although such a mechanism 144 could be utilized, it is envisioned that encasing 120 will only be positioned within first chamber area 114 for short periods of time. The sealing engagement between encasing 120 and housing 112 is sufficient to frictionally maintain the temporary position of encasing 120 within first chamber area 114.

Figure 8:
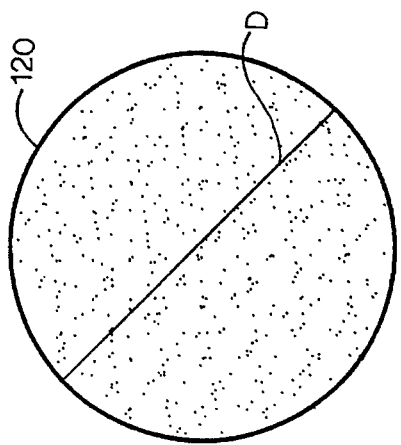

Encasing 120 is illustrated individually in FIG. 8. As seen in the figure, encasing 120 is completely tubular, and does not include free ends, similar to ends 30,32 of HME 10. The diameter D of encasing 120 is of a length sufficient to result in a significant frictional contact between encasing 120 and housing 146. This frictional contact results in the sealing engagement described above. Although not shown, encasing 20 of HME 10 could be utilized within housing 112. For this arrangement, the recoil forces of encasing 120 would force encasing 120 against housing 146 to frictionally maintain the desired positioning of encasing 120.

Also shown in FIGS. 6 and 7, a first resilient sealing ridge 164 is positioned proximate to first port 122 and intermediate first chamber area 114 and second chamber area 116. A similar second sealing ridge (not shown) is positioned proximate a second port (not shown) within surface 126. This second port is intermediate first chamber area 114 and second chamber area 116. When encasing 120 is within second chamber area 116, first resilient sealing ridge 164 and the second sealing ridge close the gap that may exist between encasing 120 and the portion of housing 146 directly proximate first port 122 and the second port. This restricts the flow of fluid entering second chamber 116 so that it passes through absorbent material 118, and not into first chamber area 114. The result is a minimization of potential dead space within housing 146. When encasing 120 is moved from one chamber area, 114 or 116, to the other, first resilient sealing ridge 164 and the second sealing ridge deflect so as to not obstruct movement of encasing 120. If desired, these sealing ridges could be utilized in conjunction with housing 196 of HME 10.

In FIGS. 9 and 10, a third embodiment HME 200 is illustrated. This HME 200 includes plunger 244 attached to encasing 220. This encasing 220 includes free ends 230,232, and it is maintained in the housing in a partially constricted manner, as discussed above. Plunger 244 does not include a pinch/catch mechanism, and the positioning of encasing 220 is maintained by its recoil forces.

It is to be understood that the present invention is not limited to the embodiments described above, but encompasses any and all embodiments within the scope of the following claims.

I claim:
1. A humidity moisture exchanger comprising:
   a housing having a first chamber area and a second chamber area, said second chamber area having means defining a first port and a second port, said housing further having a captive opening intermediate said first chamber area and said second chamber area;
   an absorbent material positioned within said housing and movable between said first chamber area and said second chamber area; and
   an encasing encircling said absorbent material, said encasing having means defining first and second openings, said first and second openings being substantially alignable with said first port and said second port, said encasing and said absorbent material both being contractible for passage through said captive opening.
2. The humidity moisture exchanger according to claim 1, wherein said encasing includes a surface substantially sealingly engageable with said housing.
3. The humidity moisture exchanger according to claim 1, wherein said encasing is substantially arcuate and includes first and second free ends movable with respect to each other.
4. The humidity moisture exchanger according to claim 1, wherein said housing further comprises at least one resilient sealing ridge intermediate said first chamber area and said second chamber area.
5. A humidity moisture exchanger comprising:
   a housing having a first chamber area and a second chamber area, said second chamber area having means defining a first port and a second port, said first chamber area and said second chamber area each being independently compressible; and
   an absorbent material positioned within said housing and movable between said first chamber area and said second chamber area.
6. The humidity moisture exchanger according to claim 5, further comprising an encasing encircling said absorbent material, said encasing having means defining first and second openings, said first and second openings being substantially alignable with said first port and said second port.
7. The humidity moisture exchanger according to claim 5, wherein said encasing includes a surface substantially sealingly engageable with said housing.
8. The humidity moisture exchanger according to claim 7, wherein said encasing is substantially arcuate and includes first and second free ends movable with respect to each other.
9. The humidity moisture exchanger according to claim 6, wherein said housing further comprises a captive opening intermediate said first chamber area and said second chamber area, said encasing and said absorbent material both being contractible for passage through said captive opening.
10. The humidity moisture exchanger according to claim 9, wherein said encasing is substantially arcuate and includes first and second free ends movable with respect to each other.
11. The humidity moisture exchanger according to claim 6, wherein said housing further comprises at least one resilient sealing ridge intermediate said first chamber area and said second chamber area.

12. A humidity moisture exchanger comprising:

a housing having a first chamber area and a second chamber area, said second chamber area having means defining a first port and a second port;

an absorbent material positioned within said housing and movable between said first chamber area and said second chamber area; and a plunger having a first end affixed to said absorbent material, said plunger further having a second end extending outward from said housing, said plunger being movable between a fully extended position and a partially extended position, said fully extended position securing said absorbent material within said first chamber area, said partially extended position securing said absorbent material within said second chamber area.

13. The humidity moisture exchanger according to claim 12, wherein said plunger is lockingly engageable with said housing.

14. The humidity moisture exchanger according to claim 12, further comprising an encasing encircling said absorbent material, said encasing having means defining first and second openings, said first and second openings being substantially alignable with said first port and said second port.

15. The humidity moisture exchanger according to claim 14, wherein said encasing includes a surface substantially sealingly engageable with said housing.

16. The humidity moisture exchanger according to claim 14, wherein said encasing is substantially arcuate and includes first and second free ends movable with respect to each other.

17. The humidity moisture exchanger according to claim 14, wherein said housing further comprises at least one resilient sealing ridge intermediate said first chamber area and said second chamber area.

18. A humidity moisture exchanger comprising:

a housing having a first chamber area and a second chamber area, said second chamber area having means defining a first port and a second port;

an absorbent material positioned within said housing and movable between said first chamber area and said second chamber area; and a substantially arcuate encasing encircling said absorbent material, said encasing having means defining first and second openings, said first and second openings being substantially alignable with said first port and said second port, said encasing having a surface substantially sealingly engageable with said housing, and said encasing includes first and second free ends movable with respect to each other.

\* \* \* \* \*